(12) United States Patent
Raftery et al.

(10) Patent No.: US 8,380,445 B2
(45) Date of Patent: Feb. 19, 2013

(54) NMR METHOD FOR DIFFERENTIATING COMPLEX MIXTURES

(75) Inventors: Daniel Raftery, West Lafayette, IN (US); Peter Sandusky, New Orleans, LA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/039,136

(22) Filed: Mar. 2, 2011

(65) Prior Publication Data
US 2011/0202285 A1  Aug. 18, 2011

Related U.S. Application Data

(63) Continuation of application No. 11/514,031, filed on Aug. 31, 2006, now abandoned.

(60) Provisional application No. 60/712,786, filed on Aug. 31, 2005.

(51) Int. Cl.
*G01N 31/00* (2006.01)
*G01N 33/48* (2006.01)
*G06G 7/48* (2006.01)
*G06G 7/58* (2006.01)

(52) U.S. Cl. ................ 702/22; 702/19; 703/11; 703/12

(58) Field of Classification Search ........................ None
See application file for complete search history.

(56) References Cited

U.S. PATENT DOCUMENTS
2005/0170441 A1   8/2005   Odunsi et al.

OTHER PUBLICATIONS

Cloarec et al. (Analytical Chemistry, 2005, 77, 517-526), published on-line Dec. 13, 2004.*
Facke et al. (Journal of Magnetic Resonance, Series A, 1995, 113, 257-259).*
Levine et al. (J. Neural Transm., 2000, 107, 843-848).*
Duarte et al. (J. Agricultural Food Chemistry, 2002, 50, 2475-2481).*
Ni et al. (J. Agricultural Food Chemistry, 1993, 41, 1026-1034).*
Zhang et al. (ChemPhysChem, 2004, 5, 794-796).*
Stoyanova et al. (Journal of Magnetic Resonance, 2002, 154, 163-175).*
Provencher (Magnetic Resonance in Medicine, 1993, 30, 672-679).*
Bax, A., Davis, D.G., "MLEV-17-Based Two-Dimensional Homonuclear Magnetization Transfer Spectroscopy," Journal of Magnetic Resonance 65, 355-360 (1985).
Belton, P.S., Colquhoun, I.J., Kemsley, E.K., Delgadillo, I., Roma, P., Dennis, M.J., Sharman, M., Holmes, E., Nicholson, J.K., Spraul, M., "Application of chemometrics to the 1H NMR spectra of apple juices: discrimination between apple varieties," Food Chem 61:1/2, 207-213 (1998).
Brescia, M.A., Kosir, I.J., Cardarola, V., Kidric, J., Sacco, A., "Chemometric Classification of Apulian and Slovenian Wines Using 1H NMR and ICP-OES Together with HPICE Data," J. Agric. Food Chem. 51, 21-26 (2003).
Cloarec, O., Dumas, M-E, Craig, A., Barton, R.H., Trygg, J., Hudson, J., Blancher, C., Gauguier, D., Lindon, J.C., Holmes, E., Nicholson, J., "Statistical Total Correlation Spectroscopy: An Exploratory Approach for Latent Biomarker Identification from Metabolic 1H NMR Data Sets," Anal. Chem. 77, 1282-1289 (2005).

(Continued)

*Primary Examiner* — Larry D. Riggs, II
(74) *Attorney, Agent, or Firm* — Bowditch & Dewey, LLP; Roger P. Zimmerman

(57) ABSTRACT

A method for differentiating complex mixtures each having one or more chemical species is provided. The method comprises producing a sample NMR spectrum by subjecting a mixture to a selective spectroscopy process, wherein the NMR spectrum has individual spectral peaks representative of the one or more chemical species within the mixture. The one or more chemical species within the mixture are identified by analyzing the individual spectral peaks, and the individual spectral peaks are then subjected to a multivariate statistical analysis.

15 Claims, 9 Drawing Sheets

OTHER PUBLICATIONS

Coen, M., Lenz, E.M., Kicholson, J.K., Wilson, I.D., Pognan, F., Lindon, J.C., "An Integrated Metabonomic Investigationo f Acetaminophen Toxicity in the Mouse Using NMR Spectroscopy," Chem. Res. Toxicol. 16, 295-303 (2003).

Degraaf, R.A., Behar, K.L., "Quantitative 1H NMR Spectroscopy of Blood Plasma Metabolites," Anal. Chem. 75, 2100-2104 (2003).

Doan, B-T., Gillet, B., Blondel, B., Beloeil, J-C., "Analysis of polyaromatics in crude gas oil mixtures: a new strategy using 1H 2D n.m.r.," Fuel, 74:12, 1806-1811 (1995).

Duarte, I., Barros, A., Belton, P.S., Righelato, R., Spraul, M., Humpfer, E., Gil, A.M., "High-Resolution Nuclear Magnetic Resonance Spectroscopy and Multivariate Analysis for the Characterization of Beer," J. Agric. Food Chem. 50, 2475-2481 (2002).

Facke, T., Berger, S., "Application of Pulsed Field Gradients in an Improved Selective TOSCY Experiment," J. Magnetic Resonance, A113, 257-259 (1995).

Holmes, E., Nicholls, A.W., Lindon, J.C., Connor, S.C., Connelly, J.C., Haselden, J.N., Damment, S.J.P., Spraul, M., Neidig, P., Nicholson, J.K., "Chemometric Models for toxicity Classification Based on NMR Spectra of Biofluids," Chem. Res. Toxicol. 13, 471-478 (2000).

Johnson, R.A., Wichern, D.W., "Applied Multivariate Statistical Analysis," Fourth Ed., Prentice Hall, Upper Saddle River, NJ, p. 8, (1998).

Kessler, H., Oschkinat, H., Griesinger, C., "Transformation of Homonuclear Two-Dimensional NMR Techniques into One-Dimensional Techniques Using Gaussian Pulses," J. Magnetic Resonance 70, 106-133 (1986).

Khandelwal, P., Beyer, C.E., Lin, Q., Schechter, L.E., Bach II, A.C., "Studying Rat Brain Neurochemistry Using Nanoprobe NMR Spectroscopy: a Metabonomics Approach," Anal. Chem. 76, 4123-4127 (2004).

Krzanowski, W.J., "Principles of Miltivariate Analysis: A User's Perspective," Oxford University Press, p. 407, (2000).

Kupce, E., Nishida, T., Freeman, R., "Hadamard NMR spectroscopy," Progress in Nuclear Magnetic Resonance Spectroscopy 42, 95-122 (2003).

Levine, J., Panchalingam, K., Mcclure, R.J., Gershon, S., Pettegrew J.W., "Stability of CSF metabolites measured by proton NMR," J. Neural Transm. 107, 843-848 (2000).

Lindon, J.C., Holmes, E., Nicholson, J.K., "Pattern recognition methods and applications in biomedical magnetic resonance," Progress in Nuclear Magnetic Resonance Spectroscopy 39, 1-40 (2001).

Lindon, J.C., Holmes, E., Nicholson, J.K., "Toxicological applications of magnetic resonance," Progress in Nuclear Magnetic Resonance Spectroscopy 45, 109-143 (2004).

Ni, Q.W., Eads, T.M., "Liquid-Phase Composition of Intact Fruit Tissue Measured by High-Resolution Proton NMR," J. Agric. Fod Chem. 41, 1026-1034 (1993).

Nicholson, J.K., Foxall, P.J.D., "750 MHz 1H and 1H-13C NMR Spectroscopy of Human Blood Plasma," Anal. Chem., 67, 793-811 (1995).

Nord, L.I., Vaag, P., Duus, J.O., Quantificationof Organic and Amino Acids in Beer by 1H NMR Spectroscopy, Anal. Chem. 76, 4790-4798 (2004).

Sandusky, P., Raftery, D., "Use of Selective TOCSY NMR Experiments for Quantifying Minor Components in Complex Mixtures: Application to the Metabonomics of Amino Acids in Honey," Anal. chem. 77, 2455-2463 (2005).

Spraul, M., Neidig, P., Klauck, U., Kessler, P., Holmes, E., Nicholson, J.K., Sweatman, B.C., Salman, S.R., Farrant, R.D., Rahr, E., Beddell, C.R., Lindon, J.C.,"Automatic reductiono f NMR spectroscopic data for statistical and pattern recognition classification of samples," J. Phar. Biom. Anal. 12:10, 1215-1225 (1994).

Stott, K., Stonehouse, J., Keeler, J., Hwang, T-L., Shaka, A.J., "Excitation Sculpting in High-Resolution Nuclear Magnetic Resonance Spectroscopy: Application to Selective NOE Experiments," J. Am. Chem. Soc. 117, 4199-4200 (1995).

Waters, N.J., Holmes, E., Williams, A., Waterfield, C.J., Farrant, R.D., Nicholson, J.K., "NMR and Pattern Recognition Studies on the Time-Related Metabolic Effects of a-Naphthylisothiocyanate on Liver, Urine, and Plasma in the Rat: An Integrative Metabonomic Approach," Chem. Res. Toxicol. 14, 1401-1412 (2001).

Williams, R.E., Jacobsen, M., Lock, E.A., "1H NMR Pattern Recognition and 31P NMR Studies with D-Serine in Rat Urine and Kidney, Time- and Dose-Related Metabolic Effects," chem. res. toxicol. 16, 1207-1216 (2003).

Zhag, F., Bruschweiler, R., "Spectral Deconvolution of Chemical Mixtures by Covariance NMR," ChemPhysChem 5, 794-796 (2004).

* cited by examiner

A  Semiselective TOCSY PCA Score Plot

B  1D Proton NMR PCA Score Plot (1.2 to 4.2 ppm)

C  1D Proton NMR PCA Score Plot (ILE Peaks Only)

A   Semiselective TOCSY Based PCA Score Plot (0.2 to 4.2 ppm)

B   1D Proton NMR Based PCA Score Plot (0.2 to 4.2 ppm)

C   **1D Proton NMR Based PCA Score Plot
Isoleucine Peaks Only – Including Methyl Peaks**

NMR METHOD FOR DIFFERENTIATING COMPLEX MIXTURES

RELATED APPLICATIONS

This application is a continuation of U.S. patent application Ser. No. 11/514,031, filed Aug. 31, 2006, which claims priority to U.S. Provisional Patent Application Ser. No. 60/712,786 filed Aug. 31, 2005, the disclosure of which are expressly incorporated herein by reference.

This invention was made with government support under grant reference numbers R01 RR018294 and R21 DK070290 awarded by the National Institutes of Health. The Government has certain rights in the invention.

TECHNICAL FIELD

The present invention is directed toward high-resolution NMR analysis of chemical structures, and more particularly to the use of selective total correlation spectroscopy ("TOCSY") to quantify and analyze a predetermined set of chemical species.

BACKGROUND OF THE INVENTION

It is well known that nuclear magnetic resonance (NMR) spectroscopy provides extremely highly detailed information on molecular structure. NMR is also quantitative because the detected signal is linearly proportional to the absolute number of active nuclei in the detected sample volume. Thus, relative numbers of hydrogen, carbon or other atoms in a molecule can be directly measured, the relative number of different molecular species in a mixture can be computed, and by using an internal standard (or even an external standard), the absolute concentration of species can be calculated.

However, when measuring the components of complex mixtures, overlapping resonances often result, which thus compromises the ability to measure concentrations quantitatively. Even small molecules often give rise to 20 or more spectral lines in the $^1H$ NMR spectrum, leading to severe overlap for many complex mixtures. For example in the $^1H$ NMR spectrum of human urine, over 1000 spectral lines can be at least partially resolved, corresponding to upwards of 100 compounds (See: J. C. Lindon, E. Holmes, and J. K. Nicholson, Prog. NMR Spec. 39, 1 (2001)).

The metabolomics approach, combining high-resolution NMR with multivariate statistical analysis, has been shown to be very powerful for distinguishing biofluid sample subpopulations based on subtle differences in the their spectra.[1,2] This approach can be widely applied to many types of samples, including urine, body fluids, and tissues. NMR based approaches are attractive because they can look at essentially all of the components of a mixture simultaneously, and thus avoid the sometimes difficult process of sample fractionation. These methods can also be rapid and quantitative.

The present invention is intended to address one or more of the problems discussed above.

SUMMARY OF THE INVENTION

The present teachings are directed to a method for differentiating complex mixtures each having one or more chemical species. The method comprises producing a sample NMR spectrum by subjecting a mixture to a selective spectroscopy process, wherein the NMR spectrum has individual spectral peaks representative of the one or more chemical species within the mixture. The one or more chemical species within the mixture are identified by analyzing the individual spectral peaks, and the individual spectral peaks are then subjected to a multivariate statistical analysis.

In another aspect of the present invention, a method for quantifying one or more chemical species within a complex mixture is provided. The method comprises subjecting a first mixture to a total correlation spectroscopy analysis to produce a first spectrum composed of individual spectral peaks representative of the one or more chemical species within the first mixture. A second spectrum is acquired from an isolated standard sample from a second mixture, the second spectrum being produced by subjecting the second mixture to a second total correlation spectroscopy analysis. The first spectrum is then compared to the second spectrum to quantify the one or more chemical species within the first mixture.

In yet another aspect of the present invention, a method for quantifying one or more chemical species within a complex mixture is provided. The method comprises subjecting the mixture to a first total correlation spectroscopy analysis to produce a first spectrum composed of individual spectral peaks representative of the one or more chemical species within the first mixture. A second spectrum is acquired from an isolated standard sample within the mixture, the second spectrum being produced by subjecting the mixture to a second total correlation spectroscopy analysis. The first spectrum is then compared to the second spectrum to quantify the one or more chemical species within the mixture.

The attached claims recite at least some of the novel aspects of the present teachings. Other advantages may well be apparent to one of skill in the art upon consideration of the description of the invention and claims contained herein.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

Figure 1:
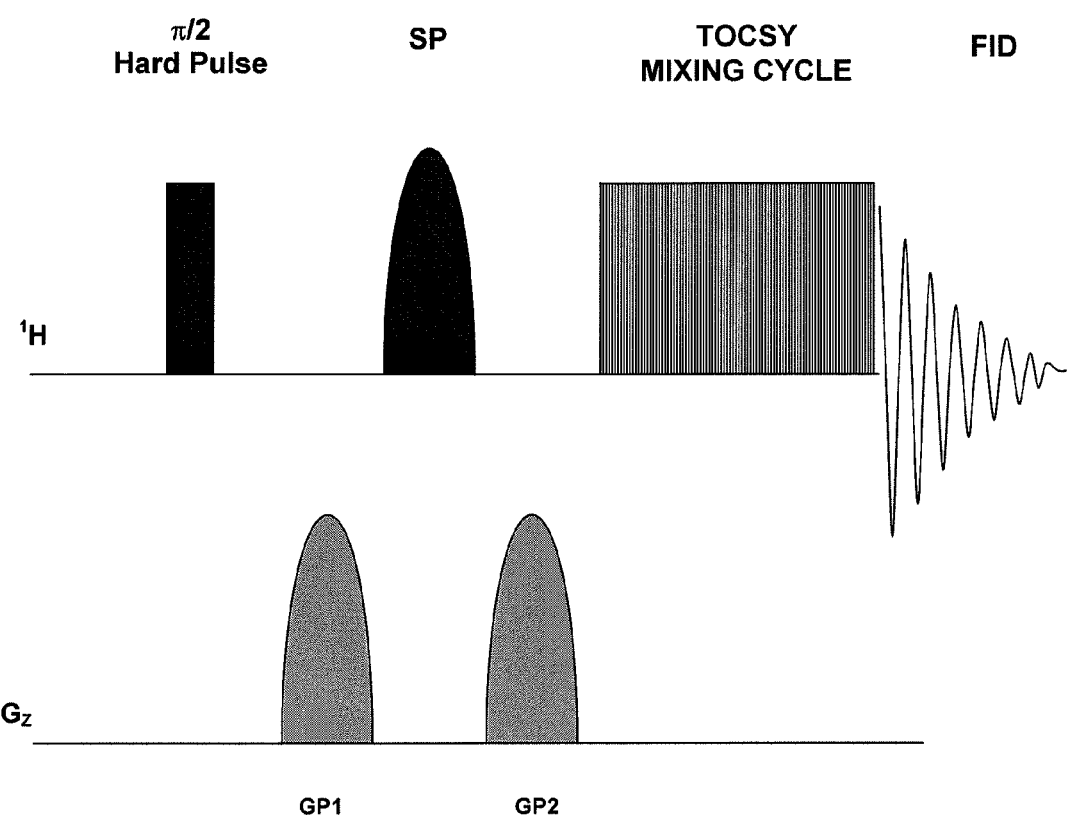
FIG. 1 shows a representative selective TOCSY pulse sequence, wherein the duration of the shaped pulse, designated "SP," was varied to produce the data presented in FIGS. 2 and 3.

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

An experimental selective total correlation spectroscopy (TOCSY) method for quantifying several chemical species of honey is described herein (see also a recently published study[3] which was authored by the present inventors and is hereby incorporated by reference in its entirety). It has been discovered that this TOCSY method is a useful alternative to the standard metabonomic analysis of biofluids. According to this method, a selective excitation pulse and TOCSY mixing period were used to focus the statistical analysis of a few pre-selected components in honey, such as amino acids for instance. Through this analysis, it was discovered that the discrimination of subpopulations in a set of samples is substantially improved, particularly as the signals used, come almost exclusively from components that vary significantly between samples. One aspect of this method is that it facilitates the accurate quantification of a predetermined set of chemical species, regardless of whether these species are major or minor components of the mixture. As such, a set of chemical compounds to be studied in a metabonomic analysis may then be chosen based on their metabolic or pharmacological significance. For instance, a specific subset of chemical compounds present in a biofluid may be chosen for study because they are known to be metabolically related.

The present methods are capable of differentiating complex and largely similar mixtures by enhancing the quantitative measurement of minor components using NMR spectroscopy. Determination of the concentration of these species can be used in one of a number of multivariate statistical analyses to differentiate similar but complex mixtures, such as those found in biofluids and/or other liquids. To achieve this, the present methods involve a combination of advanced NMR methods with multivariate statistical correlations, such as the Pearson product moment correlation test, unsupervised multivariate statistical analyses, such as the principal component analysis ("PCA"), as well as supervised multivariate statistical analyses, such as the orthogonal-partial least squares-discriminate analysis ("O-PLS-DA"). Moreover, the methods are capable of detecting low concentration species, as well as analyzing a wide range of mixtures, including biofluids such as blood, urine, spinal fluid, etc., liquid foods, chemical feedstocks, such as petroleum, and so forth, where different classes of molecules are present producing complicated, overlapping spectral features. The methods may also be used to select one or more molecules in a mixture, simplify their NMR spectra, increase their detection sensitivity, allow for quantitative evaluation of those molecules, and to differentiate mixtures that differ in the concentration of these molecular species that may be minor components in the mixtures. Additionally, the methods may also be used to differentiate sick and healthy patient samples by focusing on lipids, sugars, amino acids or other such metabolites.

The present methods enhance the ability of NMR to differentiate complex mixtures, as well as cause selective excitation of certain nuclear spins and nuclear spin polarization transfer to other nuclear spins on the same molecule. The methods are also capable of identifying and quantitating molecular components by simplifying the NMR spectra of the mixture. This approach can be used to select a certain molecular species, or several species, simplify their NMR spectra, increase their detection sensitivity in the presence of a complicating matrix, and allow for quantitative evaluation of these selected molecules. The concentrations, or more typically the NMR spectra of these species, are then subjected to multivariate statistical analysis, such as principle component analysis to allow differentiation of the samples. Many types of multivariate statistical analysis can be applied once the spectra are simplified by selective excitation. While other NMR processes are available, such as LC-NMR for instance, the present TOCSY processes have significant unique advantages over these existing methods. For instance, the present methods are more rapid, since the selective TOCSY experiments require very little time or effort for sample preparation, and they avoid any possibility of differential sample fractionation, particularly since no physical separation of the mixture components is involved.

The use of quantitative selective excitation (selective) TOCSY, and multivariate statistical analysis can be very useful to differentiate otherwise very similar samples. For instance, in the above-referenced publication, the inventors differentiated 8 different honey samples based on the concentrations of their amino acid content. The concentrations of these amino acids are typically 200 times less than the major components, α-glucose, fructose, other sugars and water.

One challenge in using processes such as selective TOCSY to detect single molecular species within complex mixtures is that such processes can produce the simultaneous excitation of several molecular spin systems at once. When this happens, problems with the purity of the individual TOCSY peaks observed and/or with their assignment into specific spin systems can occur. While it is in principle possible to use very selective excitation approaches in order to address this problem, unfortunately in most cases, greater spin system selectivity can only be gained at the expense of sensitivity. This is an unacceptable trade-off when dealing with biofluid samples. To eliminate this challenge, the present inventors have discovered an alternative two-stage modification process to the basic selective TOCSY system. At an initial stage, using a less selective excitation in the TOCSY pulse sequence optimizes the sensitivity and data collection efficiency of the experiment, at the expense of spin system selectivity. At a second stage, application of the Pearson product moment correlation coefficient method to the TOCSY peak integral intensities provides a test for individual TOCSY peak purity, and allows for the assignment of the peaks into spin systems.

Another known challenge of NMR and metabolomics analysis approaches is that in many biofluids of interest (such as urine and blood serum), only a fraction of the NMR spectral features of the different chemical species are capable of being resolved. For instance, the selective TOCSY process can behave "semiselectively" when applied to these mixtures, wherein a single selective TOCSY spectrum will very often contain peaks from several different chemical species. Using human and rat urine as examples of typical biofluid samples, the present inventors examined and compared two different solutions to this problem. Longer shaped pulse durations in the selective TOCSY pulse sequence were found to narrow the selective excitation band, thus focusing the experiment more selectively on individual chemical species. However, increasing the shaped pulse duration resulted in a significant decrease in the intensity of the TOCSY peaks, which also affects the sensitivity. Alternatively, it was discovered that relatively short excitation pulse durations can be used to produce a spectrum composed of more intense TOCSY peaks. This results in a "semiselective" TOCSY spectrum in which the TOCSY peaks will, in general, derive from several different chemical species. While initially problems may be encountered when identifying which chemical species are represented by a particular TOCSY peak, or whether a given TOCSY peak represents any single species, the judicious application of the Pearson product moment correlation coefficient method can be used to resolve these problems.[4,5] Statistical correlation methods provide a good means to identify related peaks and even molecules in metabonomics studies, as was recently shown by Nicholson and coworkers.[6] A major issue in classical metabonomics studies is the discriminating power of the method when minor components are the significant varying species. Classical metabonomic studies usually employ complete 1D proton NMR spectra as data inputs for PCA calculations.[7-14] Because of significant spectral overlap in samples such as urine or serum, the practical limit of detection is relatively high and thus discrimination of similar samples is challenging. It was found that the using semiselective TOCSY spectra as PCA data inputs is more sensitive and reliable than the classical metabonomic approach when dealing with small differences in complex biofluid compositions. In essence the coupling inherent in the NMR spectrum can be used as a filter to lower the threshold of detection for discriminating different sample subpopulations.

Additionally, it is possible to "multiplex" the selective excitation process by using an approach called Hadamard Transform NMR.[20] In Hadamard NMR spectroscopy, the peaks of interest are irradiated selectively using a frequency-domain multiplex scheme. With this approach, there is no loss in sensitivity per unit time. Hadamard matrices are used to determine the multiplexed irradiation frequencies and are then used to decode the NMR spectra as they are being processed. Most types of NMR experiments can be implemented in this fashion, as long as the frequencies of the signals of interest are known in advance. Multidimensional NMR experiments can be implemented using Hadamard principles, leading to large time savings. This approach then, because of its inherently quantitative nature, can be combined with multivariate statistical analysis such that it can be used to differentiate complex samples.

Advantages and improvements of the processes of the present invention are demonstrated in the following examples. The examples are illustrative only and are not intended to limit or preclude other embodiments of the invention.

EXAMPLES

NMR Samples

L-Amino Acids and TSP (sodium 3-trimethylsilyl (2,2,3, $3^2H_4$) i-propionate) were purchased from Sigma-Aldrich (St. Louis, Mo.) and used without further purification. For NMR analysis, amino acid solutions were prepared in 50 mM phosphate buffer at pH 7. Human urine was collected from the volunteers. A sample of urine collected from a male adult Sprague-Dawley rat was the generous donation of Dr. Peter Kissenger and Dr. Chester Duda of Bioanalytical Systems, Inc. (West Lafayette. IN). For NMR analysis, urine samples were prepared by the addition of 60 μl of 1 M phosphate buffer, pH 7, to 540 μl of neat urine. For the PCA study, urine samples were collected at three time points during the day, and these samples were split into thirds, forming 9 samples, 6 of which were spiked with varying concentrations of isoleucine. All NMR samples were run in 5 mm tubes with 10% added $D_2O$ (Cambridge Isotopes Laboratory, Inc.) and 50 μl TSP.

NMR Spectroscopy:

NMR spectra were taken on a Bruker AVANCE DRX 500 MHz spectrometer (Bruker-Biospin, Fremont, Calif.), using a 5 mm inverse HCN triple resonance probe equipped with XYZ axis gradient coils. All spectra were acquired at 25° C., and were referenced to the TSP methyl peak at 0.00 ppm. Proton spectra were acquired using a 1D NOESY pulse sequence incorporating presaturation for water suppression during the relaxation delay and mixing time.[15,16] The relaxation delay and mixing times were set to 2 s and 300 ms, respectively, and the presaturation power used was the minimum needed to effect complete suppression of the water peak. In order to achieve high signal-to-noise ratios for minor components, 64 FID transients were averaged, resulting in a total acquisition time of 7 min. Selective TOCSY experiments used the standard pulse sequence found in the Bruker XWINNMR pulse program library (see FIG. 1), and consists of a hard 90° pulse—z gradient—selective 180° pulse—z gradient train to achieve selective excitation of the target peak, followed by a MLEV-17 TOCSY spin lock.[17-19] It should be understood that the pulse sequence shown in FIG. 1 illustrates one example of carrying out a selective TOCSY experiment. Many choices exist for the selective pulse and the mixing cycle, and in some experiments, the first pulse can be eliminated. Here, gaussian-shaped pulsed z-field gradients were 1 ms in duration and 14 mT/m at maximum strength. Secant-shaped selective 180° pulses were found to be most effective for selective excitations. The duration of the shaped pulse was varied as described below. TOCSY mixing times were 70 ms. Thirty-two 16K point FID transients were averaged in each selective TOCSY experiment, resulting in an acquisition time of 1 min. The "spdisp" utility incorporated in the Bruker XWINNMR software package was used to determine shaped pulse excitation frequency band widths. 1 Hz line broadening was used in processing the spectra. It should be appreciated and understood that the parameters included herein are for illustrative purposes only, wherein other types of selective pulses, mixing cycles and mixing times may be employed by those skilled in the art while still encompassing the scope of the present teachings. As such, the present teachings are not intended to be limiting herein.

Pearson Product Moment Experiments:

A series of 64 random numbers with a mean value of 1.00 and a standard deviation of 0.25 was generated using the Microsoft EXCEL random number utility (Microsoft Corp., Redmond, Wash.). Negative values in the list of random numbers were discarded, and the first 27 values of the remaining numbers were used as random mM concentrations of leucine, isoleucine and valine added to nine aliquots of a single human urine sample. In this way, nine NMR samples of human urine with random concentrations of leucine, isoleucine and valine were produced. Selective TOCSY spectra taken on this set of samples were processed and transformed using the same parameters, and the TOCSY peaks over the resulting set of nine spectra were base-line corrected and then integrated as a set using the XWINNMR multiple integration macro written in-house. The same chemical shift limits were used for all spectral integrations. The resulting text file containing the relative integral intensities was read into a Microsoft EXCEL spread sheet, and the matrix of numbers used as input data for Pearson product moment correlation coefficient calculations performed using the EXCEL utility.

PCA Calculations:

For the isoleucine spiking PCA study, nine human urine samples (three controls and six spiked with 250±65 µM isoleucine) were prepared as described above from 3 different urine samples from the same individual. 1D proton and semiselective TOCSY spectra for the nine urine samples were acquired, transformed and phased using XWINNMR. The real parts of the transformed spectra were converted to XY plot format JCAMP files. Each JCAMP file was text edited to remove header text and X data, and then read in as a column into an EXCEL spreadsheet. The 8K points of each spectrum were 4-fold binned to yield a 2K data column. In this way two 2K by nine matrices were constructed, one matrix containing the set of nine 1D proton spectra, and one matrix containing the set of nine semiselective TOCSY spectra. 298 point segments of these two matrices, corresponding to the 1.2 to 4.2 ppm chemical shift region of the spectra, were used as input data for correlation PCA calculations performed in MINITAB 13 (MINITAB Inc., State College, Pa.). The relative variance contributions of the first two principal components are indicated in the figure captions. In all cases fewer than eight principal components were found to be adequate to account for >99.9% of the variance.

The Effect of Shaped Pulse Duration:

The pulse sequence used in the selective TOCSY experiment is shown in FIG. 1.[17-19] The duration of the shaped pulse, used in this experiment in a 180° refocusing mode, and denoted as "SP" in FIG. 1, will largely determine the frequency width excited by the selective pulse sequence. In general, of course, lengthening the shaped pulse duration will narrow the excitation frequency band width. This relationship can be quantitatively evaluated using the Bruker XWINNMR "spdisp" utility.

Figure 2:
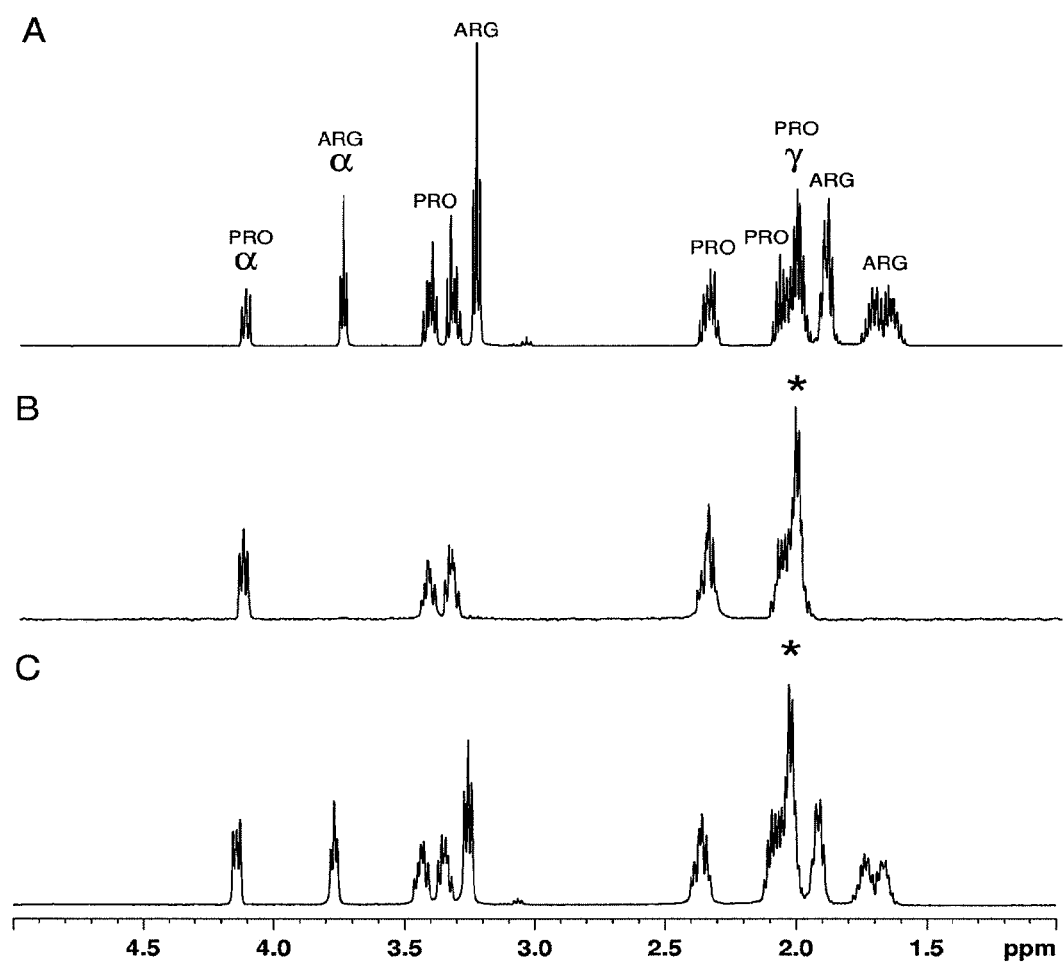
FIG. 2 shows the effect of shaped pulse duration, "SP," on the selectivity of 1D TOCSY experiment. (A) 1D proton spectrum of a mixture of 10 mM L-Proline and 10 mM L-Arginine in pH 7 phosphate buffer and 10% $D_2O$. Spectra were taken using 1D NOESY Presat sequence for water suppression. (B) Selective TOCSY spectrum of this sample with selective excitation frequency set on the proline γ peak at 2.0 ppm (*) and SP=40 ms. (C) Same experiment as shown in B, but with SP=10 ms.

A system composed of 10 mM L-arginine and 10 mM L-proline was used to examine experimentally the effects of varying the selective TOCSY sequence shaped pulse duration (FIG. 2). The results of particular interest in these experiments are the effects on the TOCSY peak intensities, a consideration of central importance if the selective TOCSY experiment is to be used for the quantitative analysis of specific chemical components of a biofluid mixture. In general the results observed when varying the shaped pulse duration will depend on the NMR spectrum of the target chemical compound. However, two general cases can be described. In cases where the target excitation peak is well separated in the spectrum from any other peak of its own spin system, the intensities of the TOCSY peaks will increase with an increase in the shaped pulse excitation frequency band width, until the excitation frequency band width equals the spectral width of the target peak. This case is illustrated by the two experiments presented in FIG. 3A. Note that for these examples the target peak width is approximately 20 Hz, corresponding to an optimal shaped-pulse duration of 40 ms.

Figure 3:
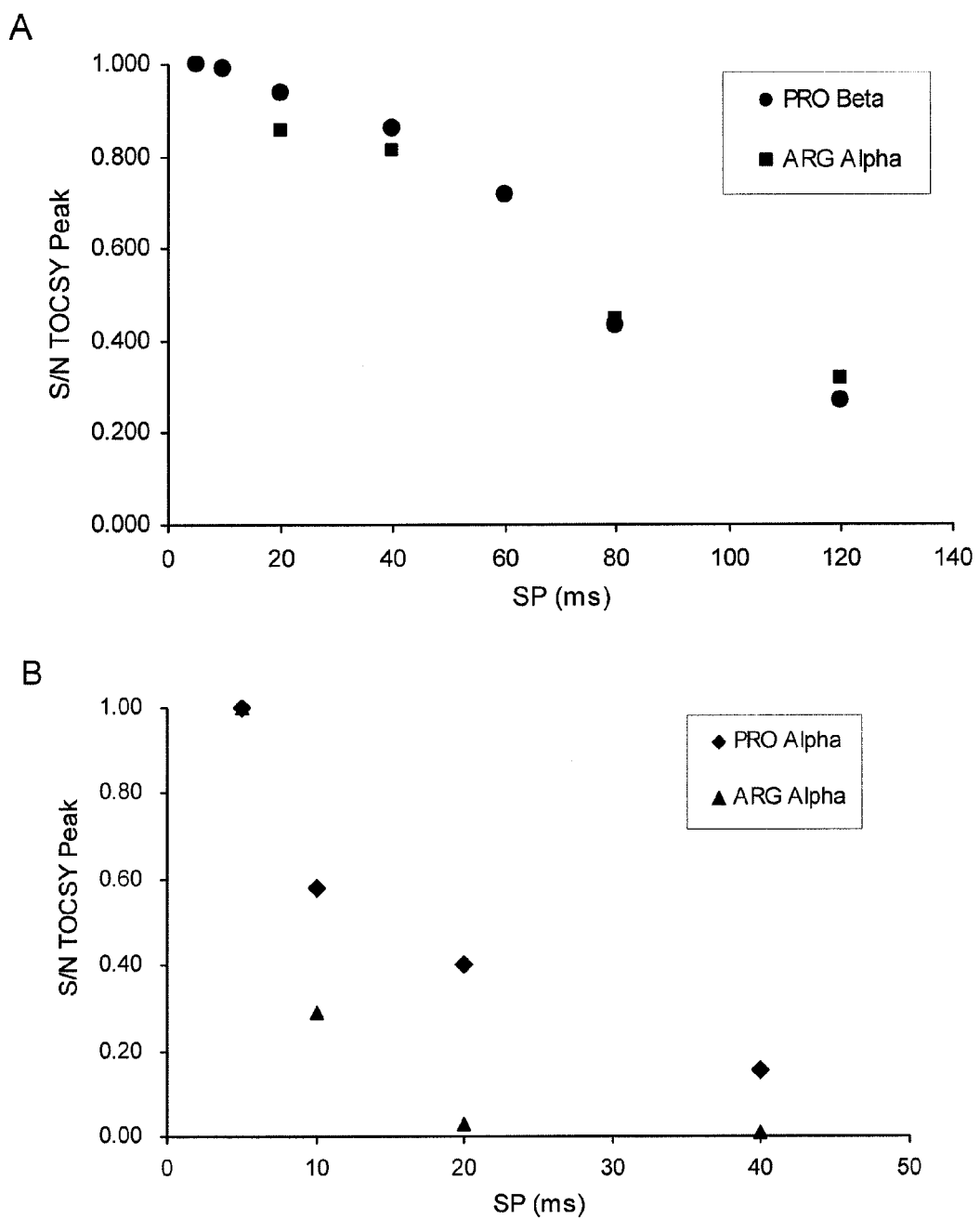
FIG. 3 shows the effect of shaped pulse duration, "SP," on the signal to noise ratio of the TOCSY peaks produced in the selective TOCSY experiment. All spectra were taken on the Proline-Arginine mixture described in FIG. 2. (A) On resonance irradiation of isolated target peaks, (•) S/N of proline β TOCSY peak (2.37 ppm) produced by selective irradiation of the proline α peak (4.15 ppm), (■) S/N of arginine α TOCSY peak (3.77 ppm) produced by selective irradiation of the arginine δ peak (3.25 ppm). (B) Effects associated with off resonance irradiation of nearby peaks, (♦) S/N of proline α TOCSY peak (4.15 ppm) produced by selective irradiation centered on the proline γ peak (2.00 ppm), (▲) S/N of arginine α TOCSY peak (3.77 ppm) produced by selective irradiation centered on the proline γ peak (2.00 ppm)

It should be noted that the simple relationship between shaped pulse duration and TOCSY peak intensity described above is observed only when the target excitation peak is well separated in the spectrum from other peaks of its own spin system. In the examples presented in FIG. 3A target peaks were 350 to 275 Hz away from the nearest neighbor peaks of their own spin systems. The second general case that can be described occurs when the target excitation peak is close to another peak of its own spin system. In this case off-resonance excitation of this second neighboring peak will increasingly occur as the shaped pulse duration is shortened. The effects of this in the selective TOCSY experiment are presented in FIG. 3B, where the signal to noise ratio of the proline α TOCSY peak is plotted as a function of the shaped pulse duration, with the shaped pulse excitation frequency centered on the proline γ peak (♦). The proline γ peak width is approximately 56 Hz, which should correspond to an optimal selective-pulse duration of 14 ms. However, the proline β2 peak occurs only 13 Hz down field from the proline γ peak. Consequently as the shaped pulse duration centered on the proline γ peak is shortened below 10 ms dramatic increases in the proline α TOCSY peak intensity are observed, due to the off resonance excitation of the proline β2 peak. Concurrently strong arginine peaks are also observed in the TOCSY spectrum due to the off-resonance irradiation of arginine γ peak (FIG. 3B—▲). The experiment has become "semiselective."

When discussing the quantitative results to be expected from the selective TOCSY experiment, it is obvious that each spin system in a mixture constitutes its own special case. However, all spin systems show an increase in TOCSY peak intensity when the shaped-pulse duration is shortened. So in terms of sensitivity, it beneficial to use a relatively short, or "semiselective," shaped pulse duration. Since a shorter shaped-pulse duration will in general excite more spin systems at the same time, shorter pulse durations are also more efficient in terms of surveying the chemical species present in a biofluid sample.

Figure 4:
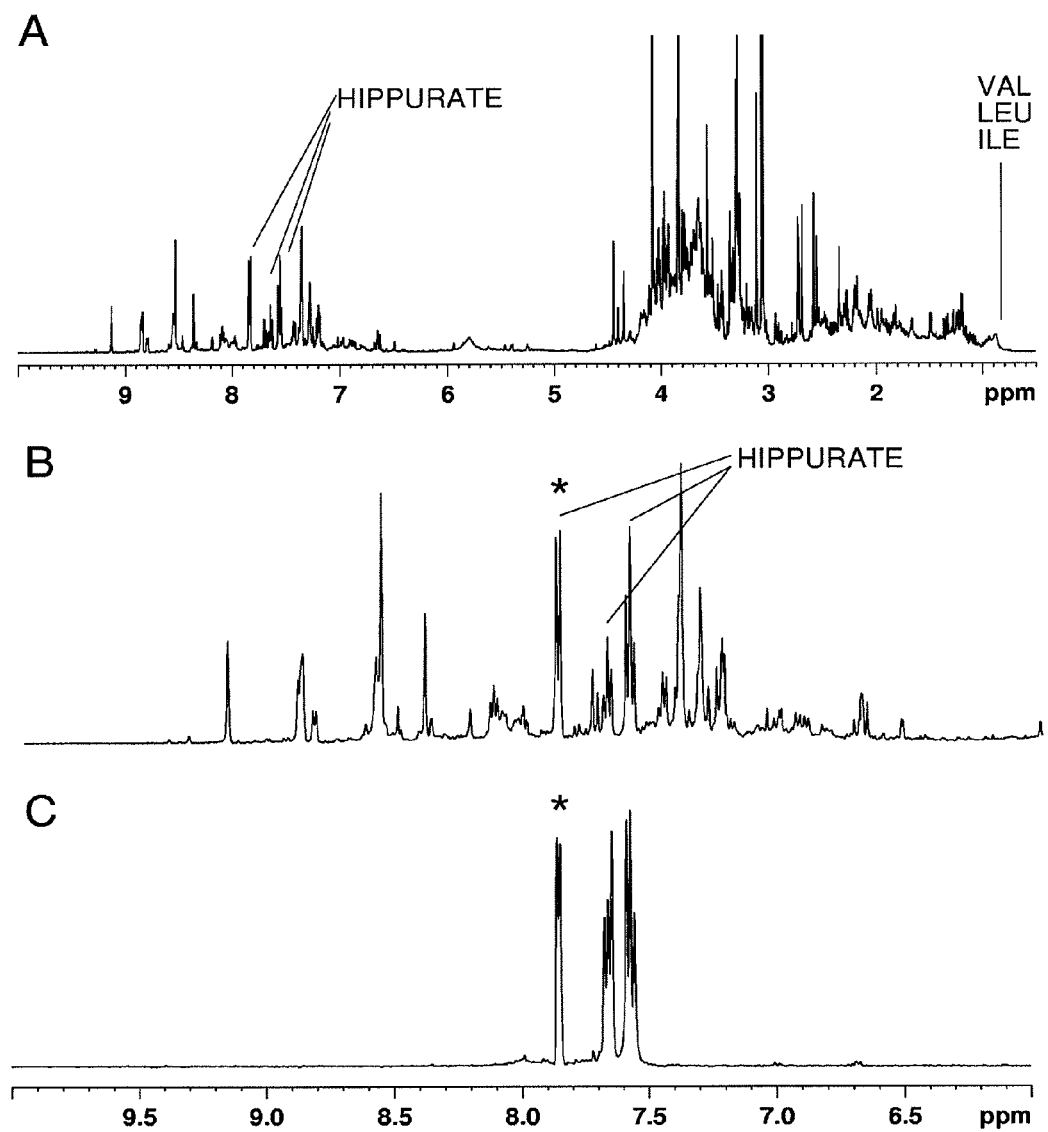
FIG. 4 shows (A) Proton NMR spectrum of rat urine acquired using the 1D presat NOESY sequence to achieve water suppression. (B) Low field expansion of the rat urine proton NMR spectrum. (C) Selective TOCSY of rat urine with the selective pulse frequency set on the hippurate 7.88 ppm peak (*), and acquired with SP=10 ms.
Figure 5:
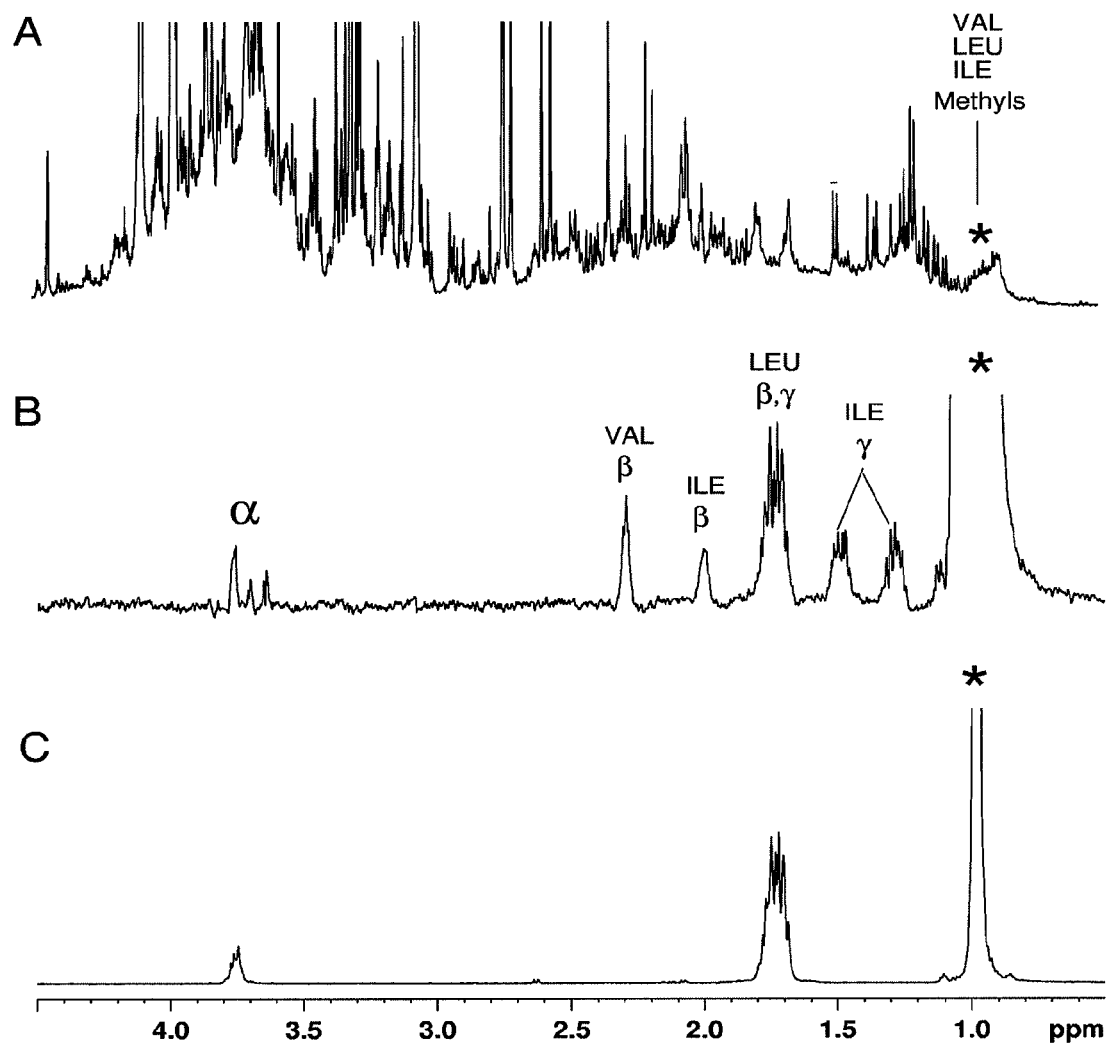
FIG. 5 shows (A) High field expansion of the proton NMR spectrum of human urine spiked with 1 mM each of leucine, isoleucine and valine. Spectrum was acquired using the 1D presat NOESY sequence to achieve water suppression. (B) High field expansion of the selective TOCSY spectrum of the spiked human urine sample from A with the selective pulse frequency set on the leucine-isoleucine-valine methyl peaks around 1.00 ppm (*), and acquired with SP=10 ms. (C) Selective TOCSY spectrum of a 10 mM solution of leucine with the selective pulse frequency set on the methyl peak around 1.00 ppm (*), and acquired with SP=10 ms. The C-alpha peaks appear somewhat low in intensity due to the poor efficiency of the TOCSY mixing cycle in this case.

Use of the Pearson Product Moment Method to Test the Purity of TOCSY Peaks:

In the case of urine samples, spectral overlap varies from mild to severe. FIG. 4A shows the proton spectrum of urine collected from an adult male Sprague-Dawley rat. In some cases, the selective TOCSY experiment can yield relatively pure single component spectra. An example of this is rat urine hippurate, the selective TOCSY spectrum of which is shown in FIG. 4C. More typically, excitation of any given peak in the urine spectrum will give rise to a spectrum containing peaks from several different spin systems. An example of this is shown in FIG. 5B, where excitation of the human urine amino acid methyl peak at 1 ppm yields a TOCSY spectrum containing peaks from leucine, isoleucine and valine. In either case however, regardless of whether a single spin system or multiple spin systems are excited, the separate individual TOCSY peaks, if pure, may be used to measure the concentrations of the chemical species present in the mixture.[3]

With the use of less selective excitation, or in the case of severely overlapped spectra in complex mixtures, it becomes more likely that any resolved TOCSY peak produced will contain contributions from several different chemical species. For example, it is not clear a priori that any of the urine sample TOCSY peaks resolved in FIG. 4C or 5B are pure. This of course raises the possibility that a particular TOCSY peak can no longer be accepted as an accurate measure of the concentration of a particular chemical species.

In addition, since the application of a less selective excitation pulse to a biofluid mixture also generally produces a more complex TOCSY spectrum, containing peaks from several different spin systems, it may also become difficult to assign specific peaks to specific chemical species. An example of this is the α-proton region in the human urine TOCSY spectrum shown in FIG. 5B. Here it is clear that the four TOCSY peaks resolved between 3.7 and 3.8 ppm are amino acid α-proton peaks. However which of the three target amino acids each of the four a peaks belongs to is unclear.

Fortunately, however, the Pearson product moment correlation coefficient method can be used as a statistical test to determine the purity of any particular TOCSY peak, and is also useful to help define which peaks belong to the same spin system. For two independent variables $x_i$ and $y_i$, measured in sample i over a set of samples, with average values X and Y, the Pearson product moment correlation coefficient, PM, is given by:[4,5]

$$PM = \sum_i (x_i - X)(y_i - Y) \bigg/ \sum_i \sqrt{(x_i - X)^2} \sum_i \sqrt{(y_i - Y)^2}$$

If x and y are the integral intensities of two TOCSY peaks belonging to the same spin system, and neither is significantly contaminated by peaks of another spin system, then the peak intensities of the two will be highly correlated when they are measured over a set of samples, and the PM calculated for the two peaks will be close to one. Otherwise, the correlation will be significantly diminished.

Table 1 summarizes the results from a set of experiments in which semiselective TOCSY measurements were made on a set of 9 human urine samples generated by spiking a single sample of urine with random concentrations of leucine, isoleucine and valine. Most urine samples will show widely variable amounts of these amino acids, as well as certain other unidentified species with peaks occurring near 1.00 ppm. The particular urine sample chosen for these experiments had negligible amounts of these amino acids before spiking, which allowed for good experimental control over the amounts of these three amino acids present. A single semiselective TOCSY experiment was performed on each of the 9 samples, using a 10 ms shaped pulse duration centered on the amino acid methyl peak of 1.00 ppm. The PM values calculated from the integrated TOCSY peaks in these experiments were 0.88 to 0.99 for peaks belonging to the same spin systems, and less than 0.57 for peaks belonging to different spin systems (Table 1). If any peak contained significant contamination from a spin system of a second molecule, which presumably would not be statistically related over the sample set to the target spin system, then its intra spin system PM values would be significantly reduced.

TABLE 1

Pearson Product Moment Correlation Coefficients for Aliphatic Amino Acid Semiselective TOCSY Peaks Measured in Human Urine

|  | LEU α | LEU β, γ | VAL α1 | VAL α2 | VAL β | ILE α | ILE β | ILE γ1 | ILE γ2 |
| --- | --- | --- | --- | --- | --- | --- | --- | --- | --- |
| LEU α | 1.000 | 0.916 | 0.234 | 0.326 | 0.389 | 0.397 | .424 | 0.440 | 0.469 |
| LEU β, γ | 0.916 | 1.000 | 0.484 | 0.554 | 0.576 | 0.382 | 0.292 | 0.323 | 0.320 |
| VAL α1 | 0.234 | 0.484 | 1.000 | 0.934 | 0.886 | 0.367 | 0.126 | 0.152 | 0.070 |
| VAL α2 | 0.326 | 0.554 | 0.934 | 1.000 | 0.919 | 0.204 | −0.007 | 0.056 | −0.007 |
| VAL β | 0.389 | 0.576 | 0.886 | 0.919 | 1.000 | 0.479 | 0.320 | 0.393 | 0.326 |
| ILE α | 0.397 | 0.382 | 0.367 | 0.204 | 0.479 | 1.000 | 0.901 | 0.918 | 0.887 |
| ILE β | 0.424 | 0.292 | 0.126 | −0.007 | 0.320 | 0.901 | 1.000 | 0.967 | 0.961 |
| ILE γ$^1$ | 0.440 | 0.323 | 0.152 | 0.056 | 0.393 | 0.918 | 0.967 | 1.000 | 0.994 |
| ILE γ$^2$ | 0.469 | 0.320 | 0.070 | −0.007 | 0.326 | 0.887 | 0.961 | 0.994 | 1.000 |

Using the product moment correlation coefficients listed in Table 1, it is possible to make definitive assignments of the amino acid spin systems, including those peaks in the confusing α-proton region. The three amino acids, leucine, isoleucine and valine, are ubiquitous in biofluids, and have been identified in metabonomic studies on urine,[7,8] blood plasma,[9-11] aqueous liver extracts,[10-11] brain fluid,[12] wine[13] and beer.[14] However the identification of these three amino acids in those complex mixtures has often been made based simply on the observation of proton NMR peaks near 1 ppm. While connectivity or spiking experiments have been used, they are time consuming. In contrast, the use of the fast 1D semiselective TOCSY experiment in combination with Pearson product moment correlation coefficient analysis clearly defines the unique spectral signature of a complete spin system. Thus the product moment correlation coefficient method can be used both as a test to confirm the integrity of any given TOCSY peak, and also as a means to identify the spin system and confirm the identity of the chemical species detected from multiple, correlated peaks in the spectra.

Figure 6:
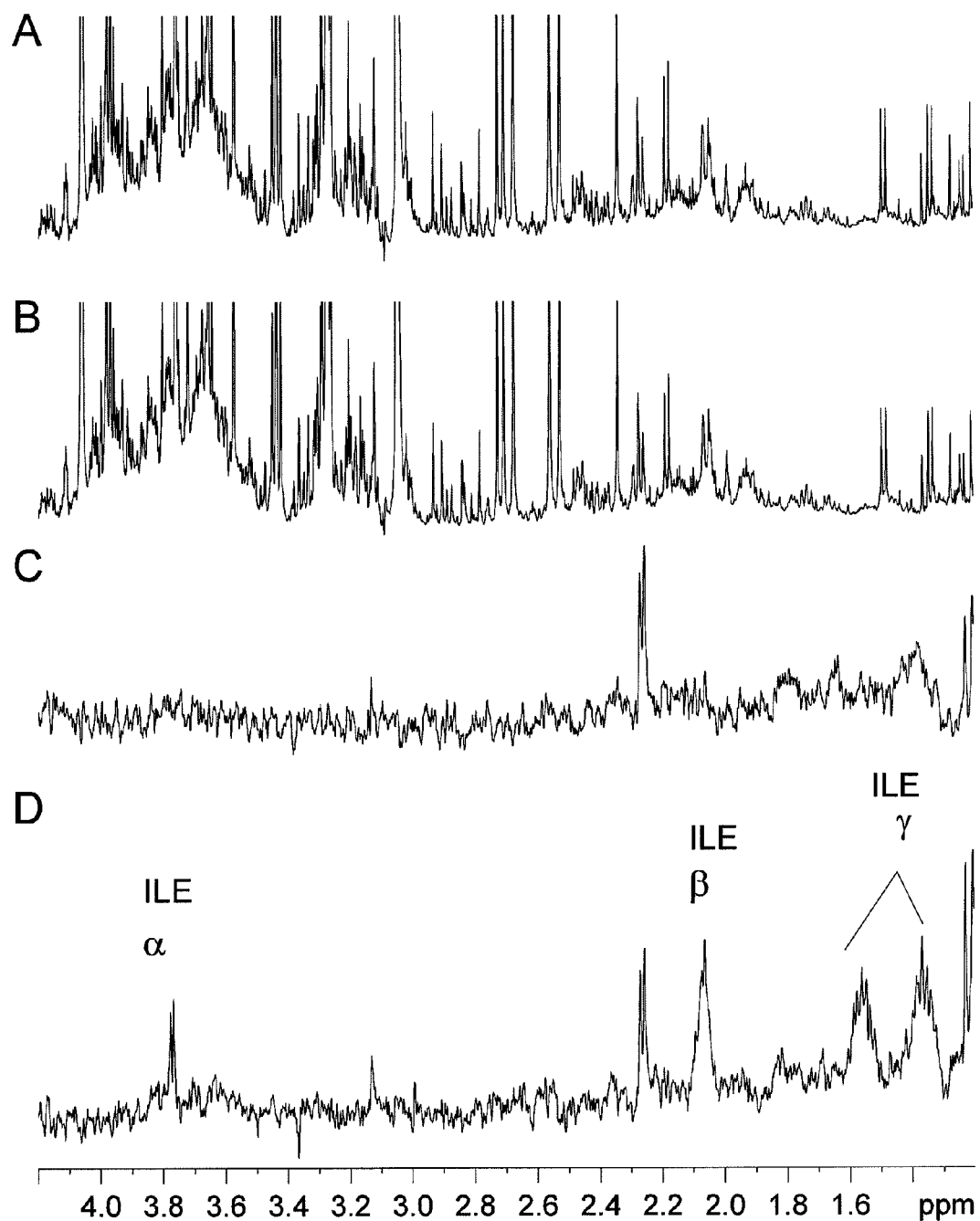
FIG. 6 shows (A) High field expansion of proton NMR spectrum of human urine. (B) High field expansion of the proton NMR spectrum of human urine sample from A spiked with 250 µM isoleucine. (C) High field expansion of semiselective TOCSY spectrum of human urine from A. (D) High field expansion of semiselective TOCSY spectrum of human urine sample from A spiked with 250 µM isoleucine. Both TOCSY spectra were taken with SP=10 msec centered at a frequency of 1.00 ppm.

A Test of the Sensitivity of Semiselective TOCSY Spectra as Data Inputs for Metabonomic PCA:

An important feature of the selective TOCSY experiment is the ability to focus the analysis of different samples on components that can be used to draw distinction between subtlely different subpopulations in sets of very similar very complex samples. An experiment was performed on human urine samples to test the ability of semiselective TOCSY to make such subtle distinctions. FIG. 6 presents 1D proton NMR and semiselective TOCSY spectra of a control human urine sample, and the same sample spiked with 250 μM isoleucine. It should be clear that addition of 250 μM isoleucine to urine produces only very subtle, almost undetectable, differences in the 1D proton NMR spectrum, as can be seen by comparing FIGS. 6A and 6B. In contrast, dramatic differences are observed in the semiselective TOCSY spectra of the spiked and control samples (FIGS. 6D and 6C).

Intuitively it would seem that the use of semiselective TOCSY spectra as data inputs for PCA calculations would make metabonomic studies more sensitive to small differences in metabolite concentrations. To test this idea, three samples of human urine were collected from a single individual over the course of a single day. Each of the three samples was divided into three aliquots, and two of the aliquots from each sample were spiked with amounts of isoleucine varying between 185 and 315 μM. The exact amount of isoleucine added to each spiked sample was determined from the first six numbers between 185 and 315 occurring in a list generated using the EXCEL random number utility. This sample preparation procedure generated a set of nine human urine samples of which six were spiked with 250±65 μM isoleucine. 1D proton spectra and semiselective TOCSY spectra, taken with the selective excitation pulse centered at 1 ppm, were acquired on each of these samples. The resulting spectra were subjected to correlation PCA calculations using the spectral region from 1.2 to 4.2 ppm. That is, the region of the complete NMR spectrum containing isoleucine peaks, exclusive of the methyl peak at 1 ppm that was used for the selective excitation (see additional discussion below).

Figure 7:
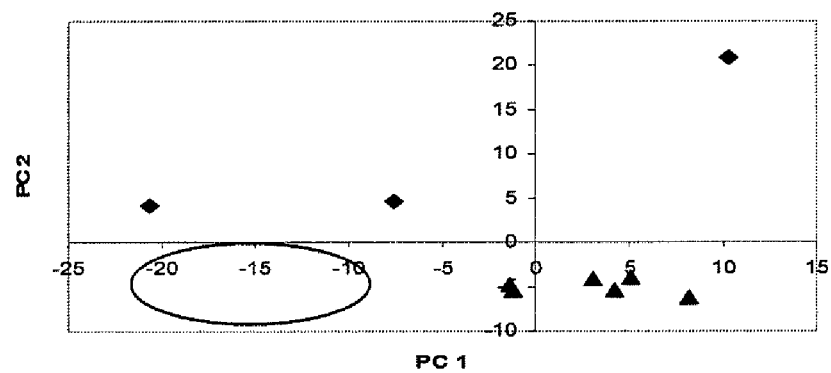
FIG. 7 shows PC1 vs. PC2 score plots from the isoleucine spiking study of human urine. (A) Score plot from PCA calculated using 298 bins of the semiselective TOCSY spectra as data inputs (1.2 to 4.2 ppm data with selective excitation at 1.00 ppm). (B) Score plot from PCA calculated using 298 bins of the 1D proton spectra as data inputs (1.2 to 4.2 ppm). (C) Score plot from PCA calculated using the 57 bins of the 1D proton spectra containing isoleucine peaks (exclusive of the methyl peaks near 1.00 ppm) ▲=isoleucine spiked, ◆=control. PC1 and PC2 account for 56.3% of the total variance in (A), 90.0% in (B) and 93.4% in (C)
Figure 7:
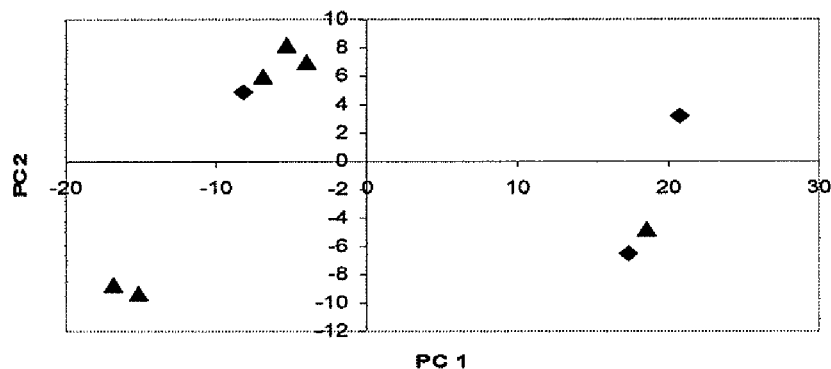
Figure 7:
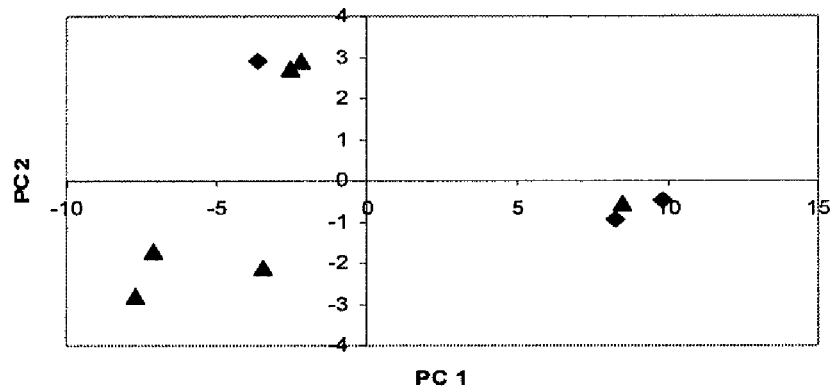

The PC1 vs. PC2 PCA score plots shown in FIG. 7 clearly indicate the advantage of the semiselective TOCSY approach. The score plot calculated using the semiselective TOCSY spectra as data inputs shows a clear discrimination between the spiked and control samples (FIG. 7 A). In contrast, the PCA score plot calculated using 1D proton NMR spectra as data inputs does not discriminate between the isoleucine spiked and control samples (FIG. 7B). Rather, the clustering observed in the PCA score plot calculated using 1D proton spectra is random, and does not derive either from the origin of the urine nor from the spiking of the samples. The correct clustering is dramatically improved using the selective TOCSY approach. It is also interesting to note that the discrimination is largely along PC2. We found that PC1 was in fact dominated by (chemical) noise due to the variation of the many components among the different urine samples.

As an alternative, it is possible to use the 1D proton spectra as data inputs but use only on those frequency bins that include the isoleucine signals. In this third PCA calculation, data inputs were limited to the 57 bins of the 1D proton spectra containing the isoleucine α peak, at 3.65 to 3.75 ppm, β peak, at 1.95 to 2.05 ppm, γ1 peak, at 1.45 to 1.55 ppm, and γ2 peak, at 1.25 to 1.35 ppm. However, this approach also fails to produce any clean score plot discrimination between the spiked and control samples (FIG. 7C).

Figure 8:
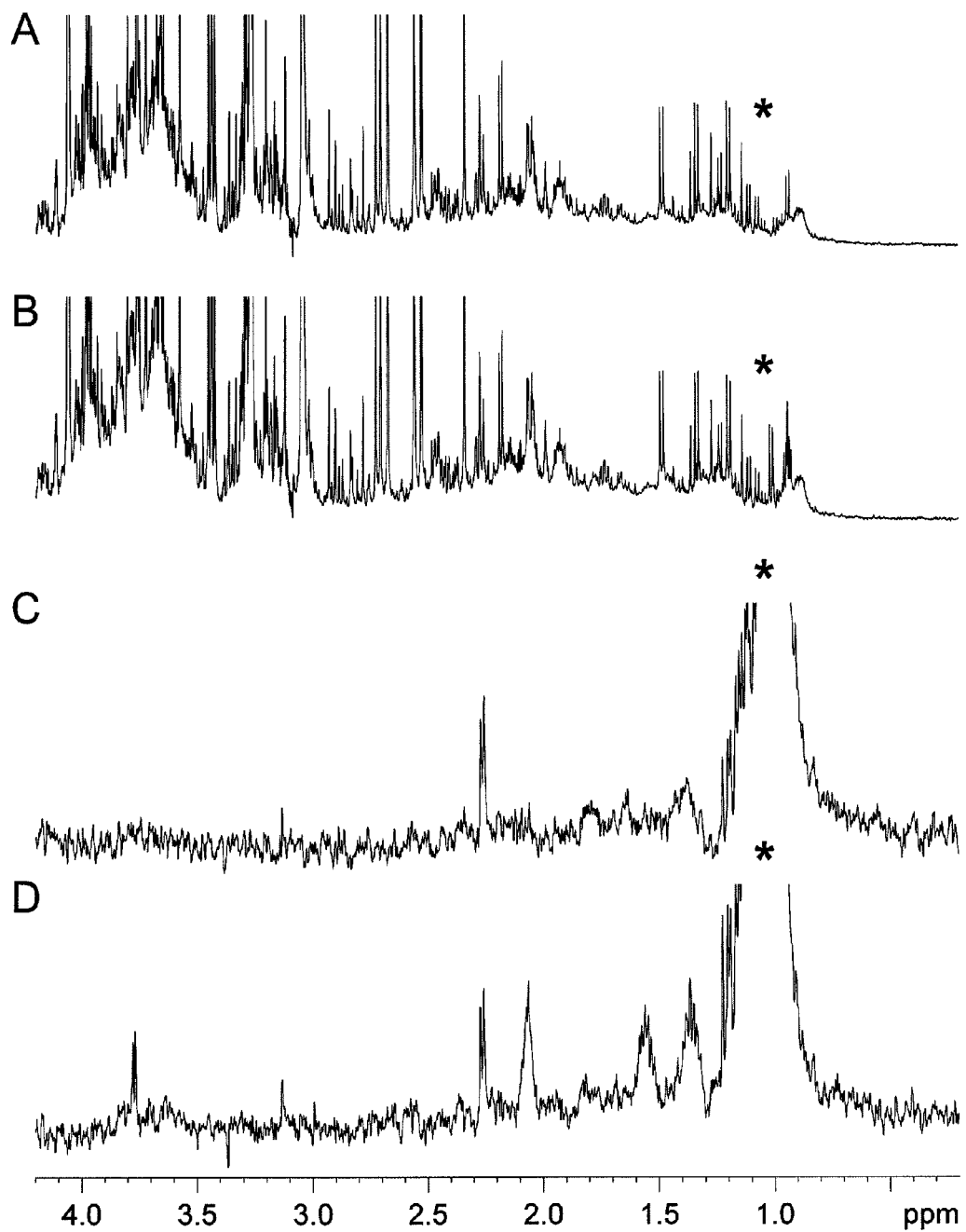
FIG. 8 shows (A) High field expansion of proton NMR spectrum of human urine. (B) High field expansion of the proton NMR spectrum of human urine sample from A spiked with 250 µM isoleucine. (C) High field expansion of semiselective TOCSY spectrum of human urine sample from A. (D) High field expansion of semiselective TOCSY spectrum of human urine sample from A spiked with 250 µM isoleucine. Both TOCSY spectra were taken with SP=10 msec centered at a frequency of 1.00 ppm (*)
Figure 9:
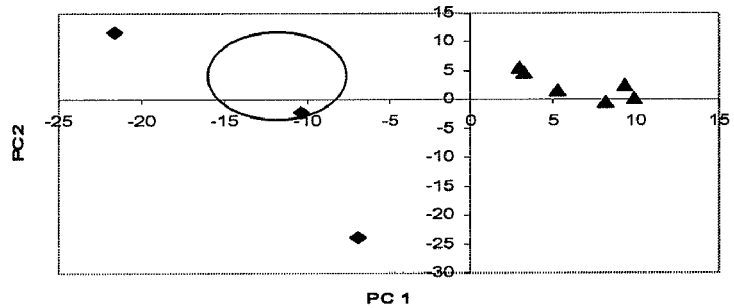
FIG. 9 shows PC1 vs PC2 score plots from an isoleucine spiking study of human urine. (A) Score plot from PCA calculated using 398 bins of the semiselective TOCSY spectra as data inputs (0.2 to 4.2 ppm data with selective excitation at 1.00 ppm). (B) Score plot from PCA calculated using 398 bins of the 1D proton spectra as data inputs (0.2 to 4.2 ppm data). (C) Score plot from PCA calculated using the 129 bins of the 1D proton spectra containing isoleucine peaks (including methyl peaks at 0.90 to 1.1 ppm) ▲=isoleucine spiked, ◆=control.
Figure 9:
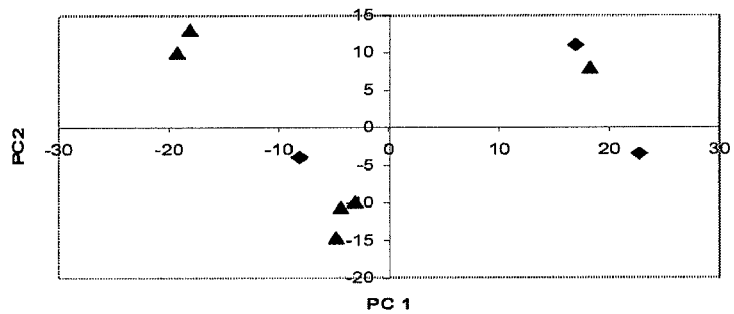
Figure 9:
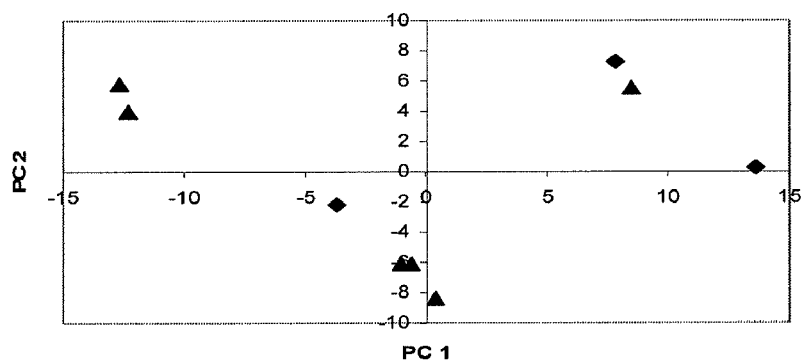

The most intense peaks of the isoleucine spectra are γ and δ methyl peaks found between 0.90 and 1.1 ppm. These peaks were used as the selective TOCSY target peaks in the isoleucine spiking study, and were excluded from the PCA calculations presented in FIG. 7. In fact inclusion of these intense methyl peaks in the PCA calculation has very little effect on the quality of the spiked vs. control clustering observed in the resulting PCA score plots (see FIGS. 8 and 9). The clustering produced in the selective TOCSY spectra based calculations remains very good (FIG. 9A), while no actual discriminatory clustering is produced in the 1D proton based calculations (FIGS. 9B and 9C). Thus the calculations, both exclusive and inclusive of the isoleucine methyl peaks, demonstrate that the selective TOCSY approach is more sensitive to small differences in metabolite concentration, or less intense spectral features, than the standard metabonomics approach.

It should be noted that the above procedure, introduction of complete selective TOCSY spectra as PCA data inputs, was performed in this particular case only as a test of the greater discriminatory sensitivity of the semiselective TOCSY spectra relative to 1D proton spectra. In practice, in an actual metabonomics study, the selective TOCSY peaks for a number of compounds of interest would be integrated, and the integral intensity numbers used as PCA data inputs.[3] The use of the peak integral intensities is preferable in that it facilitates more rapid statistical analysis, allows for the testing of the TOCSY peaks for purity using the Pearson correlation method, and allows for the establishment of the statistical significance of the different chemical components using MANOVA.[3]

The use of semiselective TOCSY spectra as data inputs for PCA calculations provides a relatively rapid means of distinguishing between sets of biofluid samples with subtle differences in metabolite concentrations. When multiple components are excited by the semiselective pulse, the Pearson moment correlation coefficient provides a method to distinguish pure TOCSY peaks and to aid in their assignment. Finally, the use of semiselective TOCSY spectra as PCA data inputs is more sensitive to small differences in metabolite concentrations than PCA calculations using 1D proton spectra as data inputs. Good separation of spiked and control samples could be made easily at the level of 250 μM with the use of selective TOCSY using a 1 min acquisition time.

It should be understood and appreciated that additional external standardization processes, such as electronic quantitating methods (e.g., ERETIC), may also be used in addition to and/or in conjunction with the selective TOCSY processes of the present teachings. As such, the present teachings are not intended to be limiting in nature herein.

While exemplary embodiments incorporating the principles of the present teachings have been disclosed hereinabove, the present teachings are not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCES

The following are incorporated herein by reference in their entirety:
(1) Lindon, J. C.; Holmes, E.; Nicholson, J. K. *Prog. Nucl. Magn. Reson. Spec.* 2001, 39, 1-40;
(2) Lindon, J. C.; Holmes, E.; Nicholson, J. K. *Prog. Nucl. Magn. Reson. Spec.* 2004, 45, 109-143;
(3) Sandusky, P. O.; Raftery, D. R. *Anal. Chem.* 2005, 77, 2455-2463;
(4) Johnson, R. A.; Wichern, D. W. *Applied Multivariate Statistical Analysis*, 4th Edition, Prentice Hall, Upper Saddle River, N.J., 1998;
(5) Krzanowski. W. J. *Principles of Multivariate Analysis: A User's Perspective*. Revised Edition, Oxford University Press. Oxford, 2000;
(6) Cloarec, O.; Dumas, M.-E.; Craig, A; Barton, R. H.; Trygg, J.; Hudson, J.; Blancher, C.; Gauguier, D.; Lindon, J. C.; Holmes, E.; Nicholson, J. K. *Anal. Chem.* 2005, 77, 1282-1289;
(7) Holmes, E.; Nicholls, A W.; Lindon, J. C.; Connor, S. C.; Connelly, J. C.; Haselden, J. N.; Damment, S. J. P.; Spraul, M.; Neidig, P.; Nicholson, J. K. *Chem. Res. Toxicol.* 2000, 13, 471-478;
(8) Williams, R. E.; Jacobsen, M.; Lock, E. A. *Chem. Res. Toxicol.* 2003, 16. 1207-1216;
(9) de Graaf, R. A; Behar, K. L. *Anal. Chem.* 2003, 75, 2100-2104;
(10) Waters, N. J.; Holmes, E.; Williams, A; Waterfield, C. J.; Farrant, R. D.; Nicholson, J. K *Chem. Res. Toxicol.* 2001, 14, 1401-1412;
(11) Coen, M; Lenz, E. M.; Nicholson, J. K; Wilson, I. D.; Pognan, F.; Lindon, J. C. *Chem. Res. Toxicol.* 2003, 16, 295-303;
(12) Khandelwai, P; Beyer, C. E.; Un, Q.; Schechter, L. E.; Bach II, A C. *Anal. Chem.* 2004, 76, 4123-4127;
(13) Brescia, M. A; Kosir, I. J.; Caldarola, V.; Kidric, J.; Sacco, A *J. Agric. Food Chem.* 2003, 51, 21-26;
(14) Nord, L. I.; Vaag, P.; Duus J. O. *Anal. Chem.* 2004, 76, 4790-4798;
(15) Nicholson, J. K; Foxall, P. J. D. Spraul, M.; Farrant, R. D.; Lindon, J. C. *Anal. Chem.* 1995, 67, 793-811;
(16) Belton, P. S.; Colquhoun, I. J.; Kemsley, E. K; Delgadillo, I.; Roma, P.; Dennis, M. J.; Sharman, M.; Holmes, E.; Nicholson, J. K.; Spraul, M. *Food Chemistry* 1998, 61, 207-213;
(17) Kessler, H.; Oschkinat, H.; Griesinger, C.; Bermel, W. *J. Magn. Reson.* 1986, 70, 106-133;
(18) Stott, K.; Stonehouse, J.; Keeler, J; Hwang, T.-L.; Shaka, A J. *J. Am. Chem. Soc.* 1995, 117, 4199-4200; and
(19) Bax, A; Davis, D. G. *J. Magn. Reson.* 1985, 65, 355-360.
(20) E. Kupce, T. Nishida, and R. Freeman, Prog. NMR Spec. 2003, 42, 95-122.

What is claimed is:

1. A method for quantifying one or more chemical species within a complex mixture, comprising:
    subjecting a first mixture to a total correlation spectroscopy analysis to produce a first 1D NMR spectrum composed of individual spectral peaks representative of the one or more chemical species within the first mixture;
    acquiring a second 1D NMR spectrum from an isolated standard sample from a second mixture, the second spectrum being produced by subjecting the second mixture to a second total correlation spectroscopy analysis;
    quantifying the one or more chemical species within the first mixture by comparing the first spectrum to the second spectrum; and
    subjecting the individual spectral peaks of the first mixture to a multivariate statistical analysis.

2. The method of claim 1, further comprising optimizing the duration of an excitation pulse during the spectroscopy analysis of the first mixture to maximize sensitivity.

3. The method of claim 1, wherein the first mixture comprises a biofluid mixture.

4. The method of claim 1 wherein the multivariate statistical analysis comprises a Pearson product moment correlation test.

5. The method of claim 1, wherein the multivariate statistical analysis comprises a principal component analysis process.

6. The method of claim 1, wherein the multivariate statistical analysis comprises an orthogonal-partial least squares-discriminate analysis.

7. The method of claim 2, wherein the duration of the excitation pulse is about 5 to about 40 ms.

8. The method of claim 1, further comprising classifying the individual spectral peaks by applying a frequency-domain multiplex scheme.

9. The method of claim 8, wherein the frequency-domain multiplex scheme comprises a Hadamard Transform NMR matrix.

10. The method of claim 1, further comprising using the multivariate statistical analysis to determine purity of the individual spectral peaks and to assign the individual spectral peaks into spin systems.

11. The method of claim 1, further comprising differentiating the complex mixture by analyzing the concentrations of the chemical species quantified during the total correlation spectroscopy analysis.

12. The method of claim 1, further comprising optimizing a mixing pulse during the spectroscopy analysis of the first mixture.

13. A method for quantifying one or more chemical species within a complex mixture, comprising:
    subjecting the mixture to a first total correlation spectroscopy analysis to produce a first 1D NMR spectrum composed of individual spectral peaks representative of the one or more chemical species within the mixture;
    acquiring a second 1D NMR spectrum from an isolated standard sample within the mixture, the second spectrum being produced by subjecting the mixture to a second total correlation spectroscopy analysis;
    quantifying the one or more chemical species within the mixture by comparing the first spectrum to the second spectrum; and
    subjecting the individual spectral peaks of the first mixture to a multivariate statistical analysis.

14. The method of claim 13, wherein the multivariate statistical analysis comprises a Pearson product moment correlation test.

15. The method of claim 13, wherein the mixture comprises a biofluid mixture.

* * * * *